United States Patent [19]

Mosenson

[11] Patent Number: 5,620,654
[45] Date of Patent: Apr. 15, 1997

[54] METHOD AND EQUIPMENT FOR SANITIZATION OF MEDICAL WASTE

[75] Inventor: Beni Mosenson, Kiryat Tivon, Israel

[73] Assignee: Moledet, Kfar Bnei Brith, Moshav Shitufi Paklai Ltd., Moledet, Israel

[21] Appl. No.: 369,533

[22] Filed: Jan. 5, 1995

[30] Foreign Application Priority Data

Jan. 10, 1994 [IL] Israel .......................................... 108311

[51] Int. Cl.[6] ...................................................... A62D 3/00
[52] U.S. Cl. ................................. 422/28; 422/3; 588/205; 588/218; 588/900
[58] Field of Search .................................. 588/205, 900, 588/218; 422/3, 28; 210/758

[56] References Cited

U.S. PATENT DOCUMENTS

| | | | |
|---|---|---|---|
| 3,386,668 | 6/1968 | Shepherd | 241/46 |
| 3,926,379 | 12/1975 | Dryden et al. | 241/69 |
| 4,269,364 | 5/1981 | Moriconi et al. | 241/36 |
| 5,064,124 | 11/1991 | Chang | 241/33 |
| 5,078,965 | 1/1992 | Pearson | 210/760 |
| 5,116,524 | 5/1992 | Pearson | 422/3 |
| 5,217,688 | 6/1993 | Von Lersner | 422/46 |
| 5,387,350 | 2/1995 | Mason | 210/754 |

FOREIGN PATENT DOCUMENTS

| | | | |
|---|---|---|---|
| 3829380 | 3/1990 | Germany. | |
| 4138939 | 6/1993 | Germany | 588/205 |

Primary Examiner—Gary P. Straub
Attorney, Agent, or Firm—Frishauf, Holtz, Goodman, Langer & Chick

[57] ABSTRACT

Equipment for automatically sanitizing medical waste is mounted in a tightly closable housing (2) provided with charge and discharge openings (9, 10). The housing contains a shredder (20) for comminuting the inserted raw waste and for conveying the shredded material to a mixing vessel (32) where it is diluted by water and thoroughly mixed; and a container (27) for storing tubes filled with several kinds of sanitizing materials and which is configured to dispense the required number and kinds of tubes into the shredder in accordance with the pH value of the mixture in the vessel signalled to a selective valve mechanism (39) by a sensor attached to the vessel. The equipment further includes a pump (33) for recirculating liquid from the vessel to the shredder, and a pump (34) for draining fluid from the mixing vessel. A conveyor (25) conveys the sanitized waste out of the vessel and out of the housing. Electronic and control equipment is provided for operating the various components.

13 Claims, 8 Drawing Sheets

METHOD AND EQUIPMENT FOR SANITIZATION OF MEDICAL WASTE

BACKGROUND OF THE INVENTION

In most hospitals medical waste is generally collected in a central place and then treated by incineration or by grinding and heating, in order to destroy germs, noxious material and bacteria such as parthenogenic viruses. These processes are not only costly, but generate unpleasant exhaust gases and contamination of the surroundings. The present invention relates to equipment of small dimensions suitable for installing it in every hospital department, laboratory or clinic for local disposal of medical waste which includes bandages, needles and syringes, testing vials and the like. It relates particularly to a method and equipment for automatically grinding, sanitizing and neutralizing both acid and basic medical waste, and for disposing it after treatment.

PRIOR ART

Various kinds of equipment for disposal of medical waste have been designed and disclosed in patents, all using grinding and shredding of the waste material and adding a sufficient amount of sanitizing material designed to destroy germs and bacteria. The shredded material is then mixed with water which is subsequently drained and the moist waste is discharged and removed.

The following patents disclose different methods for disposal of medical waste which, however, possess not all the features necessary for obtaining an absolutely safe mass suitable for pouring it into the domestic sewage system.

U.S. Pat. No. 5,064,124 (CHANG) discloses a system for grinding, sorting and sanitizing medical waste which is characterized by a device for sorting the waste into lighter and heavier fragments. It also includes a device for returning and discharging the sanitizing liquid.

U.S. Pat. No. 4,269,364 (MORICONI) is for a needle chopping apparatus designed for disposal of needles, syringes and the like rigid medical waste by shredding it into small particles. No mention is made for sanitizing the waste before final disposal.

U.S. Pat. No. 3,926,379 (DRYDEN) discloses a destruction apparatus including a hammer mill serving to destroy disposable items and a liquid disinfecting reservoir which supplies disinfectant to a pump which discharges it into the mill. From the mill the disinfectant descends into a collecting bag provided with apertures through which the disinfectant is returned to the reservoir.

The waste disposal apparatus described in U.S. Pat. No. 3,386,668 (SHEPHERD) relates particularly to the disposal of hypodermic syringes. It includes a comminutor, means for adding liquid to the material and a porous container for receiving the comminuted material and to allow passage of the liquid through the apertures for recirculation.

DE 3829380 A1 (ORTMAYER) describes a shredder for medical waste and a separator for separating solid from liquid waste. Conveying means are provided for filling liquid and solids into separate containers which are to be hermetically closed to prevent dust from escaping into the surroundings.

None of the apparatus described are designed for conversion of medical waste into a neutral innoxious mass which can be disposed in any city dump without danger of contaminating the surroundings.

SUMMARY OF THE INVENTION

The present method of disposing of medical waste includes the following steps to be automatically carried out by the equipment:

inserting the waste and grinding it, conveying the ground material by gravity into a mixing vessel and adding water, measuring the pH-value, adding a buffer suitable for neutralizing the waste.

conveying a tube of a sanitizing material to the grinder, grinding it and conveying it by gravity into the mixing vessel, active sanitizing of the waste, draining water and conveying the waste into the domestic sewage into an internal waste container to be emptied when full.

The method may also include return of the sanitized liquid from the mixing vessel into the grinder or shredder for added cleaning.

A preferred embodiment of the equipment for carrying the above method into effect is in the form of a closed housing including the following components:

1. an inlet opening closed by a cover,
2. a motor-driven grinder or shredder of conventional design,
3. a mixing vessel containing a motor-driven stirred,
4. a motor-driven conveyor extending from the mixing vessel to the sewage system or to a waste container,
5. sensor means mounted in the mixing vessel for measuring the pH-value and electronically operated valve means for adding the correct buffer from buffer-storage containers,
6. a container for storing tubes or capsules filled with sanitizing material, provided with an automatically operated flap for dropping a tube or capsule into the grinder,
7. a pump for recirculating sanitized liquid from the mixing vessel into the grinder or shredder,
8. a pump for draining liquid from the mixing vessel,
9. electronics for operating the equipment, and
10. switching and controlling means.

As an alternative the mixing vessel may be in the shape of a rotating drum provided with means for tipping it after each complete operation for pouring the material into the sewage system.

DETAILED DESCRIPTION OF THE DRAWINGS

Figure 1:
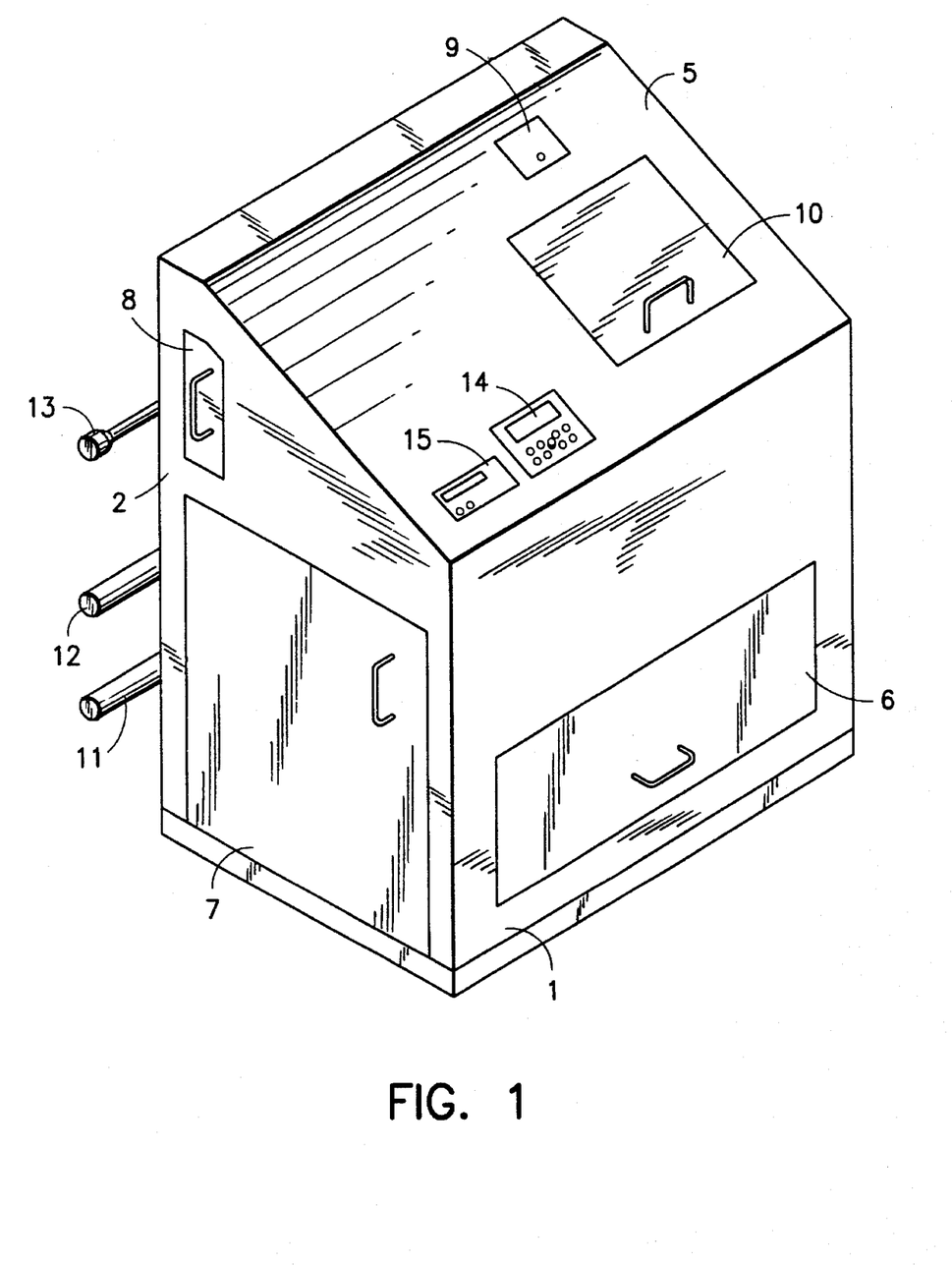
FIG. 1 is an isometric view of a housing containing apparatus for sanitizing medical waste.

The housing illustrated in FIG. 1 comprises a front wall 1, two side walls 2, a rear wall 3, a bottom 4 (the two latter visible in FIGS. 2 and 4) and a forwardly sloping top panel 5. A cover 6 closes an opening in the front wall serving for removal of sanitized waste, and a cover 7 closes a service opening in a side wall. Another closed opening 8 in the side wall serves for insertion of buffering fluid, and a closed opening 9 in the top serves for insertion of tube-packed sanitizing material, while an opening 10 in the top serves for insertion of raw waste. Pipe connections 11 and 12 serve as water inlet and outlet respectively, and number 13 denotes a cable for electric power supply. A control panel 14 and a nonobligatory printer output 15 are shown in the frontal portion of the sloping top panel.

Figure 2:
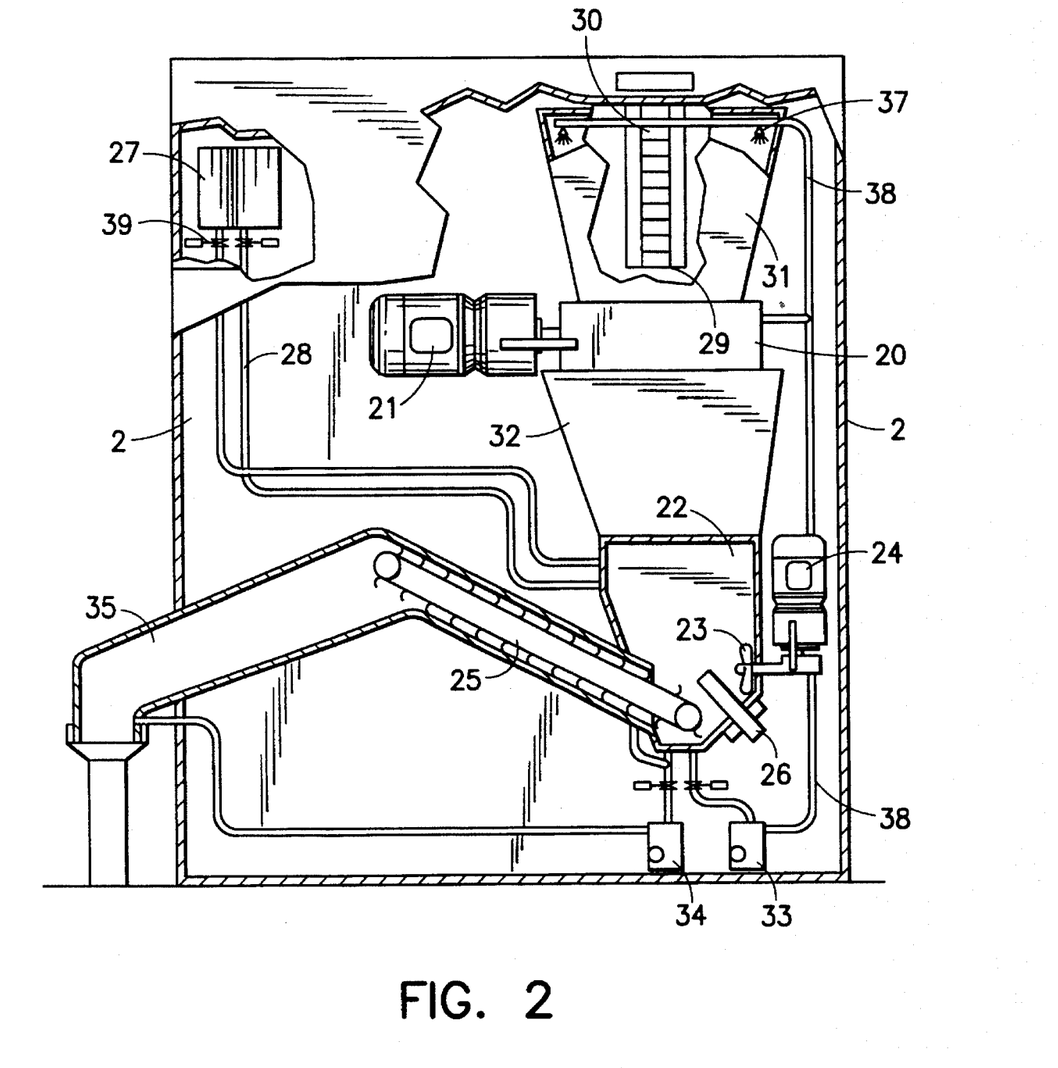
FIG. 2 is a section of the housing illustrated in FIG. 1, showing a first embodiment of the sanitizing equipment including a conveyor for removing treated waste from the mixing vessel into a domestic sewage system.

The waste treating equipment illustrated in FIG. 2 essentially includes a grinder 20 driven by an electric motor 21, a mixing vessel 22, a stirrer 23 driven by an electric motor 24 and a belt-conveyor 25, with its motor not visible in the drawing. The auxiliary equipment for neutralizing the waste comprise a pH-sensor 26, a twin vessel 27 containing buffering material and electronically controlled valve means 39 for conveying the required amount of material via piping 28 into vessel 22, in accordance with the basic or acid nature of the waste. The equipment for supplying sanitizing material into vessel 22 comprises a container 30 filled with sanitizing material enclosed in tubes or capsules of a plastic or other material which are conveyed into a hopper 31 above grinder 20 through an electronically controlled flap 29. The tubes are filled into the container through opening 9 shown in FIG. 1. Additional equipment includes a chute 32 connecting the grinder with the mixing vessel, a pump 33 for pumping sanitized and neutralized liquid through pipe line 38 into hopper 31 for spraying it into the grinder and onto the walls of the hopper for thorough disinfection. It further includes a pump 34 for supplying water to the mixing vessel and for draining liquid out of the treated waste. The conveyor lifts the material out of the mixing vessel and discharges it through funnel 35 into the main sewage system.

Figure 3:
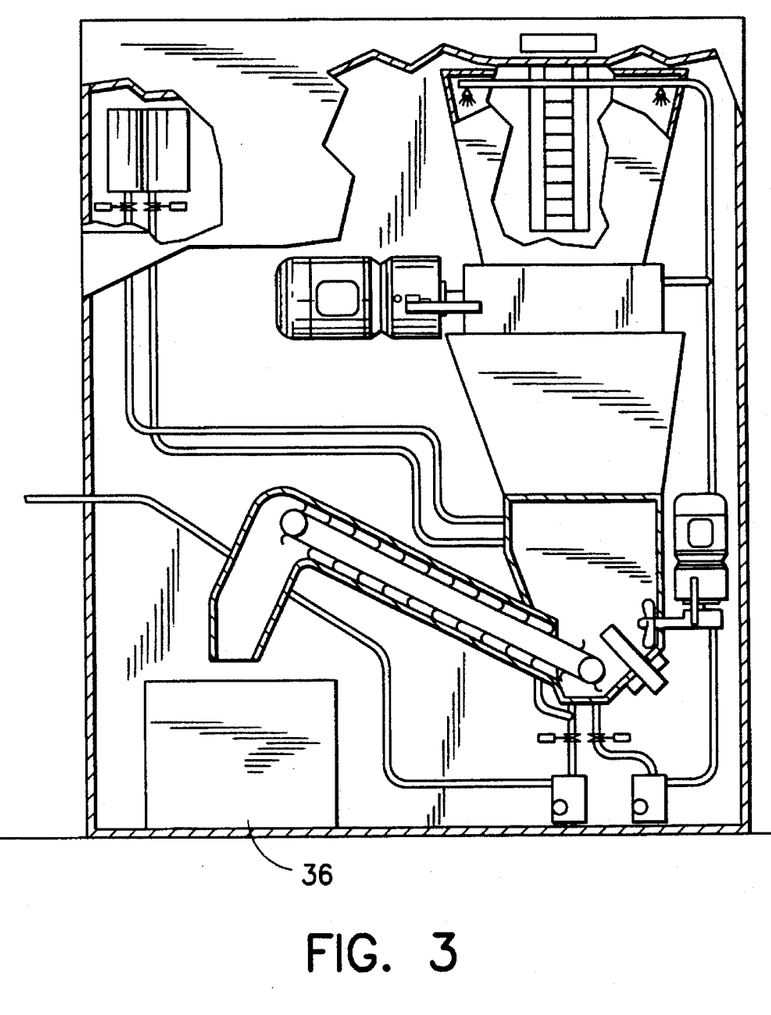
FIG. 3 is a section of the equipment illustrated in FIG. 2, showing removal of the treated waste into an internal container.

FIG. 3 illustrates the equipment which is identical with that shown in FIG. 2 with the difference that the conveyor lifts the treated waste into a container 36 which is, from time to time, lifted out of the housing through door 7 for transporting it to a central dump.

Figure 4:
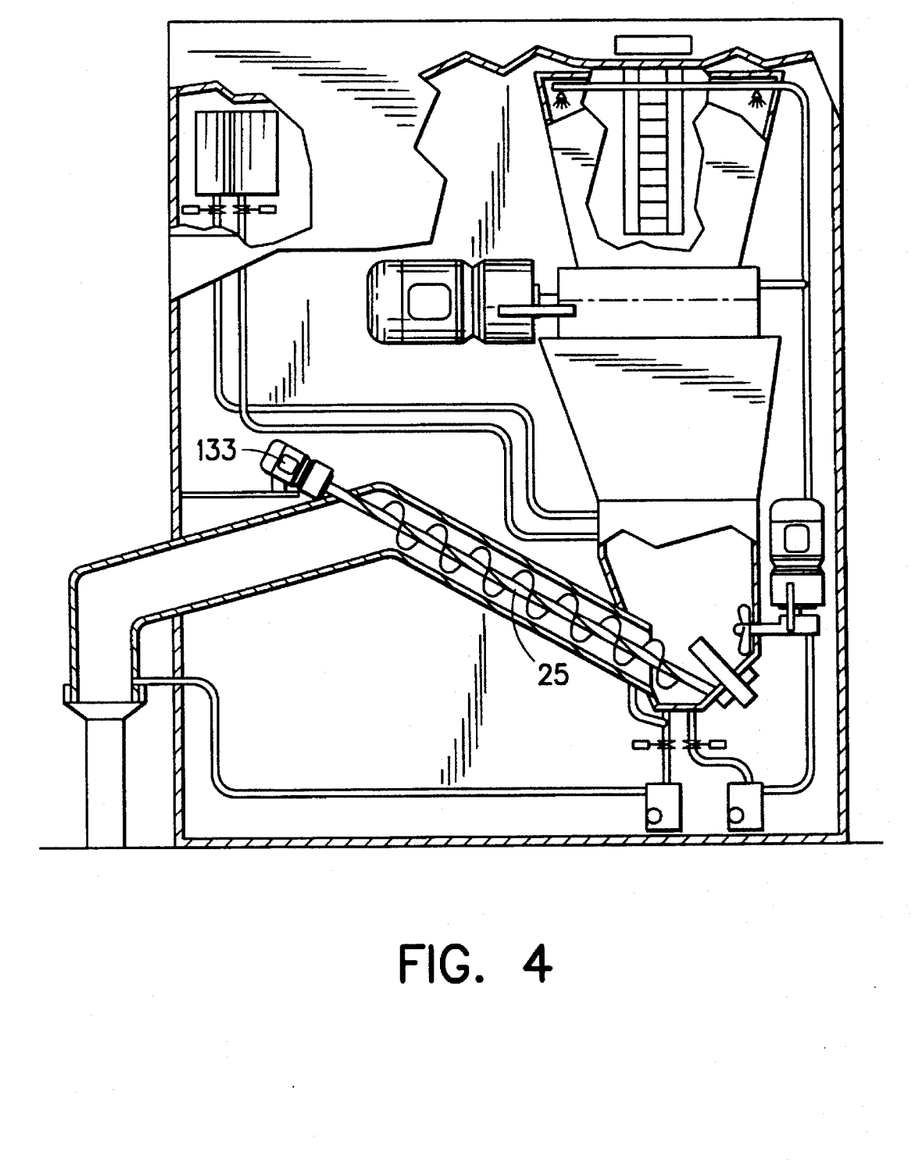
FIG. 4 is a section of the equipment illustrated in FIG. 2, including a screw conveyor for removing treated waste from the mixing vessel into a domestic sewage system.

FIG. 4 illustrates equipment which includes sanitizing and neutralizing apparatus identical with those shown in FIGS. 2 and 3 except for replacement of the belt conveyor by a screw conveyor 25' serving to lift the treated waste out of the mixing chamber and to convey it into a sewage system or an internal movable container, respectively. The conveyor is driven by an electric motor 133 adapted to rotate the conveyor in both directions, one for emptying the vessel and the other for additionally stirring the contents.

Figure 5:
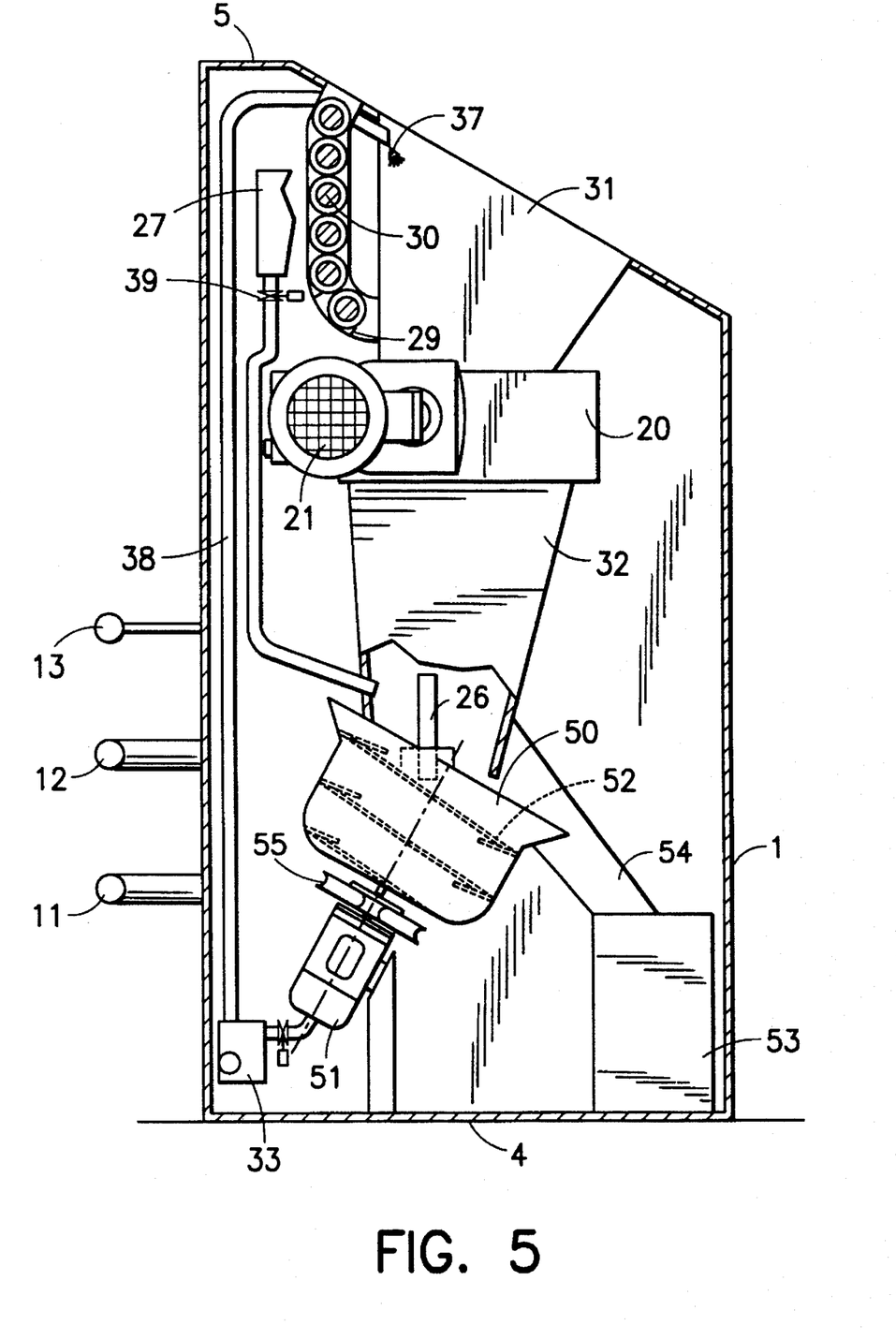
FIG. 5 is a section of equipment including a mixing chamber rotating about an inclined axis and designed for emptying by reversing its sense of rotation by means of suitably shaped blades.

FIG. 5 is a section through the housing at right angles to the sections shown in the previously described drawings and illustrating the grinder, the supply means for sanitizing and buffering liquid from another angle. Since these are identical with those described with reference to the former figures, identical numerals are being used to denote identical components in both cases. The apparatus differs from the previously described in the shape and operation of the mixing vessel 50 which is rotatably mounted on an obliquely directed support (not visible) and is driven by an electric motor 51 by means of a belt or gear 53. It can be rotated by the motor in two senses of rotation for the following purpose:—Mixing blades 52 are attached to the side wall of the mixing vessel for mixing the waste, when rotated in one direction, and for emptying the waste out of the vessel into a container 53 through a chute 54, when rotated in the other direction. A pump 33 communicates with the inside of the vessel through piping extending through the support of the vessel and serves for adding and draining water, as well as for drawing of sanitizing liquid and spreading it onto the hopper and the grinder.

Figure 6:
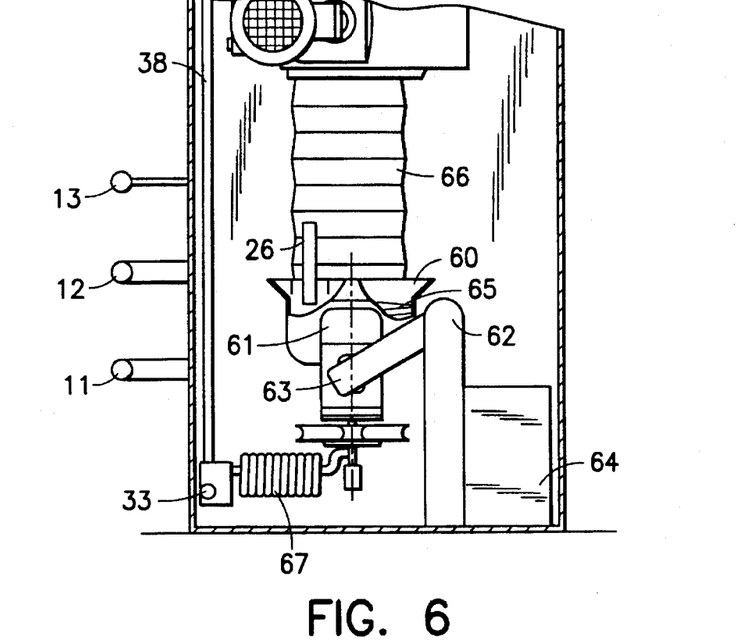
FIG. 6 is a section of equipment provided with a mixing vessel rotating about a vertical axis and with tipping means, showing the vessel in working position.
Figure 7:
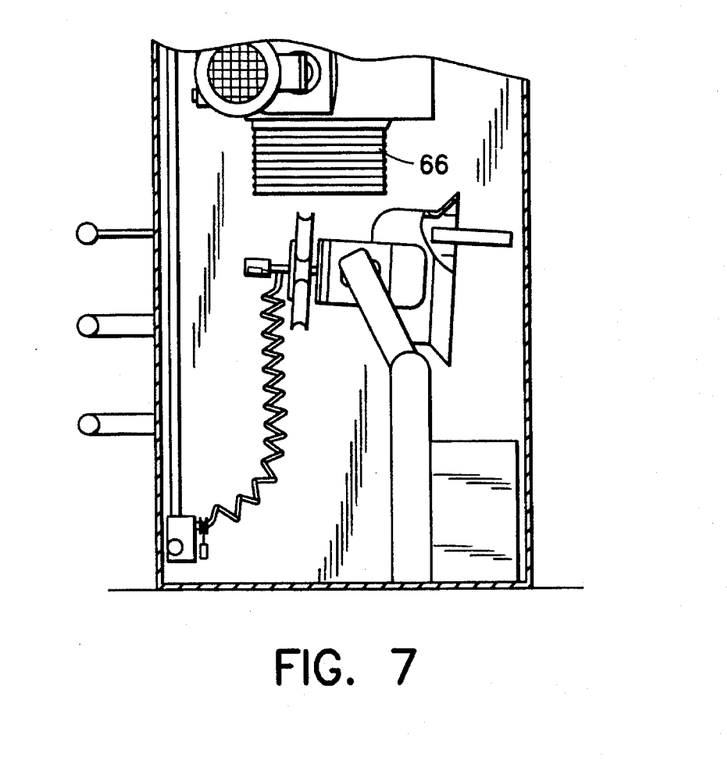
FIG. 7 is a section of the equipment illustrated in FIG. 6 showing the mixing vessel in tipped position.

Still another embodiment of the mixing vessel and its operation are illustrated in FIGS. 6 and 7 which show only the lower portion of the equipment since the components in the upper portion are identical with these in the previously described figures. Herein the mixing vessel 60 together with its driving motor 61 are normally mounted in vertical position on a horizontal axle 62 at the end of a lever 63 which can be rotated about a right angle to tip the vessel and the driving motor into horizontal position for pouring the treated waste into a container 64. It can be seen that pH-sensor 26 is likewise turned about a right angle, while being connected to electronic controls by flexible wiring. Sanitizing fluid is inserted from its reservoir direct into the grinder and buffering liquid is poured into the vessel through flexible piping (not shown) terminating above the vessel. A pump 33 serves for supplying and draining water by means of flexible piping 67 and piping extending through the support and the bearing of the vessel. The vessel is provided with stirring blades 65 attached to its side wall which also serve to empty the vessel. The waste is conveyed from the grinder into the vessel by way of a foldable hopper 66 which is to be raised (FIG. 7) when the equipment is lifted into horizontal position.

Figure 8:
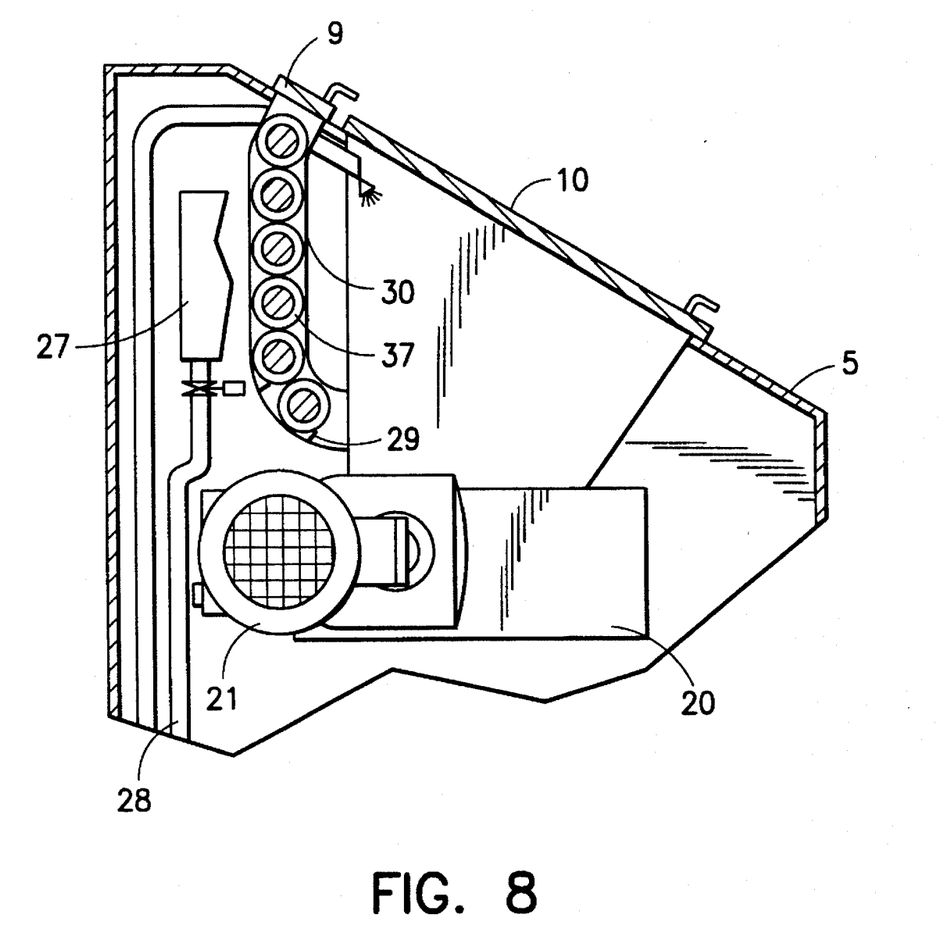
FIG. 8 illustrates a device for releasing sanitizer contained in tubes or capsules into a hopper above the shredder.

FIG. 8 illustrates, at an enlarged scale, the top of the housing including the means for supplying santizing and buffering material. The drawing shows the top cover 5 of the housing including the opening 10 for insertion of untreated waste in bags, and opening 9 for insertion of tubes or capsules 37 into a chute 30 from where they are emptied into grinder 20 by means of the openable flap 29. A vessel 27 contains two kinds of buffering liquid for neutralizing acid or basic waste respectively, which is conveyed into the mixing vessel through piping 28.

Figure 9:
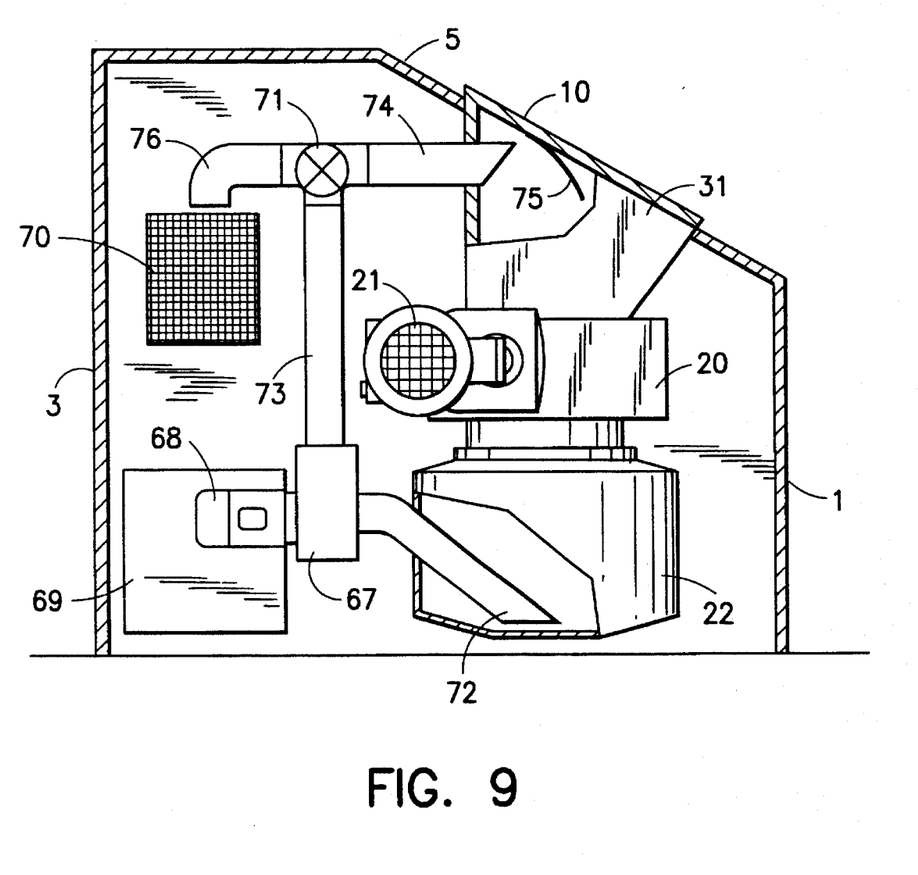
FIG. 9 illustrates another embodiment of the equipment showing a second method of stirring the waste in the mixing vessel.

The equipment illustrated in FIG. 9 contains most of the components described in the foregoing with reference to FIGS. 1 through 8, except for a different way of stirring the waste inside the mixing vessel 22. Herein the raw waste is fed to the grinder or shredder 20 through hopper 31 and drops into the mixing vessel 22 in ground condition. However, instead of stirring the waste by a mechanical stirrer 23 (FIG. 2) the water-diluted waste is drawn out of the vessel by a motor-driven centrifugal pump (67, 86) through a suction pipe 72 and is pumped back into shredder 20 by way of pipes 73, 74 and a diverter 75. The mass is directed from vertical pipe 73 into spill pipe 74 by a two-way valve 71 and is recirculated during a predesignated time period as controlled by computer means. It is automatically sanitized and treated in the manner as described in the foregoing by means of equipment which is not shown in the present drawing. After the predesignated time period for sanitizing the waste, valve 71 is automatically switched to direct the sanitized waste via pipe 76 into a removable, separating filter 70. This filter separates liquid from solid particles, the liquid flowing into a tank 69, while the solids remain in the separator for removal from time to time. Tank 69 is preferably provided with an outlet to a sewage system, the liquid being innocuous. In all other respects the equipment is similar to that illustrated in FIG. 2, except for the shape and position of the various components.

An optional feature of the apparatus is a printer adapted to issue a printed message after each operation, to the effect that all steps of the treating method were carried out in correct order.

It will be understood that the various apparatus illustrated and described in the foregoing represent examples of the many possibilities for carrying the method of disposing medical waste into effect. However, these apparatus have been designed for the present purpose with the object of occupying a minimum of space in a hospital department, a clinic or a laboratory, thus saving the task of carrying the waste to a far-away central disposal unit as is the use today.

I claim:

1. Equipment for treating and sanitizing medical waste, comprising:
   a closed housing having first closable openings for inserting medical waste and removing treated waste, and second closable openings for inserting packaged sanitizing material and buffering material, said housing enclosing:
   an electrically driven shredder connected by a hopper to a first said closable opening;
   a mixing vessel mounted below said shredder, said mixing vessel having a top connected to said shredder and being provided with an electrically powered stirrer which stirs ground waste material;
   means for adding water to said ground waste inside said mixing vessel;
   a first container which holds liquid buffer material for neutralizing basic waste;
   a second container which holds liquid buffer material for neutralizing acid waste;
   means for holding said sanitizing material;
   means for adding said sanitizing material to said shredder;
   conveying means for drawing a quantity of buffering liquid from one of said containers and conveying said quantity of buffering liquid into said mixing vessel;
   pumping means for:
      drawing liquid out of said mixing vessel and for conveying said drawn liquid into said shredder and said hopper for additional sanitizing, and
      draining liquid out of said waste in said mixing vessel;
   means for emptying said mixing vessel and for conveying emptied waste into one of (a) a sewage main and (b) a separate container; and
   electronic operating means for controlling operations of said shredder, said electrically powered stirrer, said means for adding water, said conveying means, said pumping means and said means for emptying.

2. The equipment as defined in claim 1, wherein:
   said packaged sanitizing material is divided into portions,
   each portion of said sanitizing material is enclosed in a capsule,
   a plurality of capsules are enclosed in a chute, one above the other, and
   a bottom end of said chute terminates above said shredder and is provided with a flap to be opened by solenoid means for dropping individual capsules into said shredder.

3. The equipment as defined in claim 1, wherein said mixing vessel is stationary and includes:
   a motor-driven stirrer in a side wall thereof;
   a pH-sensor in a bottom portion thereof; and
   pipe connections between said pumping means and said bottom portion.

4. The equipment as defined in claim 3, wherein the means for emptying said treated waste out of said mixing vessel comprises a screw conveyor with an inlet end thereof positioned in the bottom portion of said mixing vessel and with an outlet end thereof connected to one of said separate container and said sewage main.

5. The equipment as defined in claim 3, wherein the means for emptying said treated waste out of said mixing vessel comprises a belt conveyor with an inlet end thereof positioned in the bottom portion of said mixing vessel and with an outlet end thereof connected to one of said separate container and said sewage main.

6. The equipment as defined in claim 1, wherein a chute connects the bottom of said shredder top the top of said mixing vessel.

7. The equipment as defined in claim 5, further comprising means for issuing a printed message corresponding to operation of said equipment.

8. The equipment as defined in claim 1, further including at least one sensor means inserted into said waste inside said mixing vessel for measuring a pH-value of the waste and for transmitting corresponding signals to a processing unit.

9. The equipment as defined in claim 8, wherein said conveying means for drawing buffering liquid from one of said containers is configured to draw a quantity of buffering liquid in accordance with a signal received from said processing unit and to convey said quantity of buffering liquid into said mixing vessel.

10. Equipment for treating and sanitizing medical waste, comprising:
    a closed housing having first closable openings for inserting medical waste and removing treated waste, and second closable openings for inserting packaged sanitizing material and buffering material, said housing enclosing:
    an electrically driven shredder connected by a hopper to a first said closable opening;
    a mixing vessel mounted below said shredder, said mixing vessel having a top;
    means for adding water to said ground waste inside said mixing vessel;
    a first container which holds liquid buffer material for neutralizing basic waste;
    a second container which holds liquid buffer material for neutralizing acid waste;
    means for holding said sanitizing material;
    means for adding said sanitizing material to said shredder;
    a pump for drawing water-diluted waste out of said mixing vessel and pumping said waste to said shredder through pipe means, from where said waste is returned into said vessel by gravity;
    means for emptying said mixing vessel and for conveying emptied waste into a waste location; and
    electronic operating means for controlling operations of said shredder, said means for adding water, said pump and said means for emptying.

11. The equipment as defined in claim 10, further comprising a two-way valve inserted into said pipe means between said mixing vessel and said shredder, said valve having a first position for conveying diluted waste to said shredder and a second position for conveying treated and sanitized waste into a separator filter for separating liquid from solid waste particles.

12. The equipment as defined in claim 11, wherein liquid waste flows from said separator filter into a tank, and wherein solid waste is stored for manual removal.

13. The equipment as defined in claim 10, wherein:

said packaged sanitizing material is divided into portions, each portion of said sanitizing material is enclosed in a capsule, a plurality of capsules are enclosed in a chute, one above the other, and a bottom end of said chute terminates above said shredder and is provided with a flap to be opened by solenoid means for dropping individual capsules into said shredder.

* * * * *

UNITED STATES PATENT AND TRADEMARK OFFICE
CERTIFICATE OF CORRECTION

PATENT NO. : 5,620,654
DATED : April 15, 1997
INVENTOR(S) : MOSENSON

It is certified that error appears in the above-indentified patent and that said Letters Patent is hereby corrected as shown below:

Title page, Item [73] Assignee, after "Moledet, Israel" add: --(part interest)--.

Signed and Sealed this

Twenty-first Day of April, 1998

Attest:

BRUCE LEHMAN

Attesting Officer

Commissioner of Patents and Trademarks